(12) United States Patent
Fehér et al.

(10) Patent No.: US 8,603,537 B2
(45) Date of Patent: Dec. 10, 2013

(54) PRASUGREL CONTAINING QUICKLY RELEASED STABLE ORAL PHARMACEUTICAL COMPOSITIONS

(75) Inventors: András Fehér, Budapest (HU); Zsolt Zsigmond, Maglód (HU); Péter Tonka-Nagy, Budapest (HU); György Tibor Ujfalussy, Budapest (HU)

(73) Assignee: Egis Pharmaceuticals PLC, Budapest (HU)

( * ) Notice: Subject to any disclaimer, the term of this patent is extended or adjusted under 35 U.S.C. 154(b) by 0 days.

(21) Appl. No.: 13/437,087

(22) Filed: Apr. 2, 2012

(65) Prior Publication Data

US 2013/0259904 A1 Oct. 3, 2013

(51) Int. Cl.
*A61K 9/50* (2006.01)
(52) U.S. Cl.
USPC ........................................................ 424/493
(58) Field of Classification Search
None
See application file for complete search history.

(56) References Cited

U.S. PATENT DOCUMENTS

| | | |
|---|---|---|
| 5,288,726 A | 2/1994 | Koike et al. |
| 5,436,242 A | 7/1995 | Koike et al. |
| 6,693,115 B2 | 2/2004 | Asai et al. |
| 7,329,771 B2 | 2/2008 | Tanaka et al. |
| 2003/0134872 A1 | 7/2003 | Asai et al. |
| 2008/0176893 A1 | 7/2008 | Dziennik et al. |
| 2009/0291138 A1 | 11/2009 | Watanabe et al. |
| 2010/0004279 A1 | 1/2010 | Watanabe et al. |
| 2010/0093786 A1 | 4/2010 | Watanabe et al. |
| 2010/0179184 A1 | 7/2010 | Moon et al. |
| 2010/0280064 A1 | 11/2010 | Watanabe et al. |
| 2011/0003847 A1 | 1/2011 | Doser et al. |
| 2011/0124675 A1 | 5/2011 | Zhao |
| 2011/0201814 A1 | 8/2011 | Watanabe |

FOREIGN PATENT DOCUMENTS

| | | |
|---|---|---|
| EP | 1 728 794 A1 | 7/2001 |
| EP | 1 298 132 A1 | 4/2003 |
| EP | 2 100 606 A1 | 9/2009 |
| EP | 2 100 607 A1 | 9/2009 |
| EP | 2 100 608 A1 | 9/2009 |
| EP | 2 100 609 A1 | 9/2009 |
| EP | 2 100 610 A1 | 9/2009 |
| EP | 2 112 155 A1 | 10/2009 |
| EP | 2 415 774 A1 | 2/2012 |
| GB | 2469883 A | 11/2010 |
| WO | 2006/135605 A2 | 12/2006 |
| WO | 2008/073759 A2 | 6/2008 |
| WO | 2009/098142 A1 | 8/2009 |
| WO | 2009/129983 A1 | 10/2009 |
| WO | 2010/070677 A2 | 6/2010 |
| WO | 2010/094471 A1 | 8/2010 |
| WO | 2011/004392 A1 | 1/2011 |
| WO | 2011/027988 A2 | 3/2011 |
| WO | 2011/057593 A2 | 5/2011 |
| WO | 2011/098536 A1 | 8/2011 |
| WO | 2011/117782 A1 | 9/2011 |

*Primary Examiner* — Carlos Azpuru
(74) *Attorney, Agent, or Firm* — Millen, White, Zelano & Branigan, P.C.

(57) ABSTRACT

Prasugrel containing quickly released stable oral pharmaceutical compositions containing micronized prasugrel base, and starch or a starch derivative, and processes for the preparation thereof, and the use thereof for treating atherothrombotic events of patients suffering from acute coronary syndrome in which patients were subjected to percutaneous coronary intervention.

20 Claims, 2 Drawing Sheets

PRASUGREL CONTAINING QUICKLY RELEASED STABLE ORAL PHARMACEUTICAL COMPOSITIONS

The present invention relates to quickly released prasugrel containing pharmaceutical compositions, a process for the preparation thereof and the use of said pharmaceutical compositions together with aspirin for the prevention of atherothrombotic events of patients suffering from acute coronary syndrome, said patients having been subjected to percutant coronary treatment.

More particularly the invention is concerned with such pharmaceutical compositions containing prasugrel base as active ingredient, a process for the preparation thereof and the combined use thereof with aspirin.

Prasugrel is an effective thienopyridine structure ADP receptor inhibitor which is irreversibly bound to the P2Y12 receptor. Prasugrel has improved therapeutical properties when compared to the previously known compounds of similar effect. Similarly to clopidogrel, Effient is used in combination with aspirin for the prevention of atherothrombotic events of patients suffering from acute coronary syndrome said patients having been subjected to percutant coronary treatment/percutant coronary intervention/. Unstable angina/a serious type of thoracic pain/and heart attack belong to the disease group of acute coronary syndrome. Subcutaneous coronary surgical intervention is a type of surgery which makes the tapered coronary artery penetrable. However prasugrel inhibits the adenozin diphosphate induced aggregation more quickly and efficiently than clopidogrel. The significance of prasugrel is increased by the fact that the use of clopidogrel failed to achieve the desired result by 2-14% of the population of the US according to the warning of the FDA published in March 2010.

Prasugrel of the chemical Formula (5-/2-cyclopropyl-1-(2-fluoro-phenyl)-2-oxoethyl/-4,5,6,7-tetrahydrothieno/3.2-c/-pyridine-2-yl-acetate and the preparation thereof was described first in U.S. Pat. No. 5,288,726. The pharmaceutical composition was developed by Daiichi Sankyo Co. and is manufactured and marketed by Eli Lilly. In Europe the prasugrel containing pharmaceutical composition was authorized in 2009. The active ingredient of the authorized composition is prasugrel hydrochloride. Prasugrel is sensitive to moisture, elevated temperature and the oxygen content of air.

Several patent publications are directed to the preparation of prasugrel salts because the solubility of the base is very low on the one hand and the salts are more stable on the other.

The hydrochloric acid salt of prasugrel was first described in EP 1 298 132 B1. According to the patent specification the hydrochloric acid salt is excellently absorbed orally. In vivo pharmacological tests show that the bioavailability of the hydrochloric acid salt is much better than that of the prasugrel base. When administered in the same dose the platelet aggregation inhibitory effect of prasugrel hydrochloride was almost twice higher than that of the base. Polymorph prasugrel hydrochloride was described in WO 2011/117782 and 2010/070677.

According to US 2011/0124675 prasugrel hydrogensulfate is more stable and in pharmacological tests shows a higher bioavailability than the hydrochloride salt. The international publication contains examples describing the pharmaceutical compositions, however there are no data relating to the dissolution, bioavailability and stability of the compositions. The inventors of WO 20111/027988 state that the solubility in distilled water of the two hydrogensulfate polymorphs developed by them is higher by one order of magnitude than that of the hydrogen chloride salts. In GB 2 469 883 the polymorph III of prasugrel hydrogen sulfate was disclosed. EP 2 112 155 related to the polymorph I of prasugrel hydrogen sulfate. The patent application contains several examples showing several pharmaceutical compositions, however neither the stability nor the pharmacokinetic characteristics are disclosed.

EP 1 728 794 describes the preparation of the maleate salt. According to in vivo pharmacological tests the bioavailability of the maleate salt is even higher than that of the hydrochloride salt.

WO 2009/098142 and WO 2009/129983 are directed to the sulfonic acid salts of prasugrel. According to WO 2009/098142 the sulfonic acid salts are more stable than the hydrochloride salt both per se and in form of pharmaceutical compositions. The international publications are silent about the dissolution and bioavailability of the pharmaceutical compositions described in the examples.

In EP 2415 774 the preparation of the prasugrel hydrobromide salt and acetic acid salt solvate is disclosed. According to the patent application the hydrogen bromide salt is more readily soluble in 0.1N hydrochloric acid and also more stable than the hydrochloric acid salt. In WO 2011/004392 the polymorph of the hydrogen bromide salt of prasugrel is described together with the composition of the tablet containing the same. The dissolution and stability properties of the tablets were not disclosed either.

In WO 2011/0577953 polymorphs of prasugrel hydrobromide and hydrochloride and the preparation of salts formed with hydrogen iodide, benzene sulfonic acid, hydrogen iodide and cyclamic acid are described. The 4 months stability data of said salts are set forth as well.

Prasugrel base and salts are sensitive to moisture, elevated temperature and the oxygen content of the air. The formulation of prasugrel either in the form of the base or a salt constitutes a challenge for the pharmacist technologist.

According to EP 2 100 607 the stability of quickly released pharmaceutical compositions is improved by coating prasugrel base or a salt thereof with a water soluble layer. Although in the body of the specification prasugrel base is also mentioned, in the working examples only and exclusively prasugrel hydrochloride containing compositions are disclosed. EP 2100606 differs from the previous citation in that the coating layer is polyvinyl alcohol, carboxymethyl cellulose sodium or pullulan. In the examples the active ingredient is always the hydrochloride salt.

The compositions disclosed in EP 2 100 609 contain in addition to prasugrel as excipient lactose or mannitol having a defined particle size interval. The patent application is however silent in teaching the quality of the stability and dissolution properties. Also in this prior art the examples disclose only the preparation and testing of prasugrel hydrochloride containing compositions.

According to the examples of WO 2008/073759 prasugrel containing pharmaceutical compositions are stabilized by storing the tablets in air-and waterproof packaging. According to WO 2006/135605 the decomposition of prasugrel containing compositions can be reduced in air- and moisture-proof blister filled with inert gas. A further problem with the formulation is that the solubility and the stability of the base is significantly lower than that of the hydrochloric acid salt. This fact is substantiated by the following Table.

| pH value | Solubility of prasugrel base g/100 ml | Solubility of prasugrel HCl g/100 ml |
|---|---|---|
| pH 1 | 2.8 | 7.8 |
| pH 4.5 | 0.0035 | 0.032 |
| pH 6.8 | 0.001 | 0.007 |
| Water | 0.0009 | n.d. |

It can be seen from the above Table that the solubility of the hydrochloric acid salt of prasugrel is much higher than that of the prasugrel base even in the pH range between 4.5 and 6.8

In accordance with EP 2 100 610 the solubility of prasugrel is improved by adding LHPC. According to EP 2 100 608 tablets are prepared by grinding in the presence of HPC, croscarmellose and lactose and subsequent pressing; the dissolution is considerably improved when the duration of grinding is increased. The examples of both international patent publications relate to the preparation of prasugrel hydrochloride containing pharmaceutical compositions.

It is known from the registration file of the originator that in the prasugrel containing composition of the originator/EfientR, 5 mg and 10 mg tablets/during storage from the hydrochloride salt prasugrel base is set free. Consequently when administered together with proton pump inhibitors during storage the bioavailability of the tablet/the maximum of blood level, the Cmax value/significantly decreases as a function of the prasugrel base content. This is so because the solubility of the base formed in the tablet is considerably lower than that of the hydrochloric acid salt.

The essence of WO 2011/098536 is a process whereby micronization of prasugrel is carried out under special conditions. The main feature of said process is that micronization is performed with a mixture of prasugrel and a hydrophilic polymer i.e. in the micronization step prasugrel and a hydrophilic polymer are simultaneously present. According to this international patent publication the following hydrophilic polymers are used: hydroxypropyl methyl cellulose, hydroxypropyl cellulose, carboxymethyl cellulose, preferably the sodium or calcium salt, hydroxyethyl cellulose, polyvinyl pyrrolidone, copolymers of polyvinyl pyrrolidone, preferably copolymers comprising vinyl pyrrolidone and vinyl acetate units, polyoxyethylene alkylether, polyethylene glycol, co-block polymers of ethylene oxide and propylene oxide, polymethacrylate derivatives, polyvinyl alcohol, polyvinyl derivatives and polyethylene glycol derivatives. Since the ground composition consists of two components it is not sure whether the active ingredient shows a uniform distribution in the mixture. In case of an inhomogenous mixture it can not be taken as granted that the mixture contains the predetermined nominal amount of the active ingredient.

According the patent application wet granulation is applied. However this is always accompanied by risks when active ingredients sensitive to moisture—such as prasugrel—are used. In the examples of the international patent publication prasugrel base is used and the dissolution profile is indicated. However in order to achieve an appropriate bioavailability the dissolution is though necessary but not sufficient. The international patent application contains no data concerning the bioavailability of the prepared compositions.

It clearly appears from the aforesaid that there is a need for stable consistent quality tablets which maintain their inv vitro dissolution and in vivo bioavailability profile until the end of the expiry period.

It has been surprisingly found that the solubility of prasugrel base can be significantly improved by using micronized prasugrel base and an auxiliary agent system which is strongly hydrophilized and provides a hydrotropic environment. The tablets thus obtained can be bioequivalent with the marketed prasugrel hydrochloride containing tablets. Contrary to the composition actually on the market the dissolution and bioavailability of the composition according to the present invention does not change during storage and it can not be transformed into the less soluble form.

Needless to say that micronization of the active ingredient also plays a role in the improvement of the solubility of the prasugrel base.

Micronization belongs to the general knowledge of the person skilled in the art. In course of the preparation of the pharmaceutical composition according to the present invention we also use micronization. Our measurements carried out by means of Raman spectroscopy show that micronization was also applied in the formulation of the prasugrel hydrochloride salt i.e. in the formulation of the pharmaceutical composition of the originator. We have namely found that the characteristic particle size of prasugrel hydrochloride active ingredient of the originator is below 10 um. Thus the following conclusion can be drawn: the surprising recognition according to the present invention—namely that in spite of the large difference between the solubility of the base and the hydrochloride salt, a pharmaceutical composition being bioequivalent to the hydrochloride salt containing composition can be prepared from the prasugrel base—said recognition is to be attributed to the auxiliary agent system of the present invention exhibiting a surprisingly strong hydrotropic effect and not to the micronization step.

It has also been found that on using a strongly hydrophilized auxiliary agent which provides a hydrotropic environment there is no need of grinding the prasugrel base active ingredient together with the hydrophilic polymers. Contrary to the teaching of WO 2011/098536 a stable product of appropriate bioavailability is obtained. Thus it has been found surprisingly that the prasugrel base per se remains stable even for a storage period of 6 months.

| Stability Results | | Storage Conditions | Initial | 1 month | 2 months | 3 months | 6 months |
|---|---|---|---|---|---|---|---|
| Related substances by HPLC (%) | Dezacetyl impurity NMT 0.50% | 25 ± 2° C. 60 ± 5% RH | <0.05 | <0.05 | <0.05 | <0.05 | <0.05 |
| | | 40 ± 2° C. 75 ± 5% RH | <0.05 | <0.05 | <0.05 | <0.05 | <0.05 |

-continued

| Stability Results | Storage Period Storage Conditions | Initial | 1 month | 2 months | 3 months | 6 months |
|---|---|---|---|---|---|---|
| Any identified impurity NMT 0.15% each | 25 ± 2° C. 60 ± 5% RH | <0.05 | 0.05 | 0.07 | <0.05 | <0.05 |
| | 40 ± 2° C. 75 ± 5% RH | <0.05 | <0.05 | 0.05 | <0.05 | <0.05 |
| Any unidentified impurity NMT 0.10% | 25 ± 2° C. 60 ± 5% RH | <0.05 | <0.05 | <0.05 | <0.05 | <0.05 |
| | 40 ± 2° C. 75 ± 5% RH | <0.05 | <0.05 | <0.05 | <0.05 | <0.05 |
| Sum of impurities NMT 0.50% | 25 ± 2° C. 60 ± 5% RH | <0.05 | 0.05 | 0.07 | <0.05 | <0.05 |
| | 40 ± 2° C. 75 ± 5% RH | <0.05 | <0.05 | 0.05 | <0.05 | <0.05 |

According to the present invention as strongly hydrophilized auxiliary agent providing a hydrotropic environment starch and derivatives thereof can be used e.g. potato starch, wheat starch, maize starch, rice starch, tapioca starch, etc., or pre-gelatinized forms thereof, other starch derivatives, which are chemically modified or semi-synthetic starches, e.g. starch glycolates, e.g., sodium starch glycolate.

There are two types of sodium starch glycolate according to the USP32-NF27, i.e., Type A and Type B, which states that sodium starch glycolate is the sodium salt of a carboxymethyl ether of starch or of a crosslinked carboxymethyl ether of starch.

Pregelatinized starch is a starch that has been chemically and/or mechanically processed to rupture all or part of the starch granules. Both fully and partially pregelatinized grades are commercially available. Partial pregelatinization renders the starch flowable and directly compressible. Full pregelatinization produces a cold-water soluble starch that can be used as a wet granulation binder.

Typically, pregelatinized starch contains 5% of free amylose, 15% of free amylopectin, and 80% unmodified starch. Normally the fully pregelatinized starch contains 20-30% amylose and the rest amylopectin, which is about the same ratio (1:3) as for the partially pregelatinized form.

According to the present invention there are provided prasugrel base containing solid pharmaceutical compositions which contain in addition to the prasugrel base starch or a starch derivative and at least one further auxiliary agent. According to a preferred embodiment of the present invention the composition comprises starch, namely pre-gelatinized starch and as starch derivative sodium starch glycolate. As further auxiliary agent fillers, optionally adhesives, disintegrating agents and/or glidants can be used. As fillers water insoluble or water soluble polymers e.g. cellulose or cellulose derivatives, sugars or sugar derivatives e.g. lactose, glucose, mannitol etc. can be used. As disintegrating agent any conventional product used in pharmaceutical industry can be used e.g. crospovidone, croscarmellose or salts thereof, preferably croscarmellose sodium. As binders conventional products used in pharmaceutical industry can be used e.g. polyvinyl pyrrolidone or HPMC. As glidant preferably sodium stearyl fumarate can be used. Sodium stearyl fumarate proved to be particularly advantageous because it does not inhibit the dissolution of the active ingredient contrary to the generally used magnesium stearate. As sliding agent colloidal silica can be used. It has been found that prasugrel base is difficult to be tableted. On adding colloidal silica the tabletability can be surprisingly improved.

According to a preferred embodiment of the present invention there are provided solid pharmaceutical compositions in tablet form.

According to a still more advantageous embodiment of the present invention there are provided coated tablets particularly coated with a water soluble coating agent.

According to a particularly preferred embodiment of the present invention there are provided tablets comprising 2-5%, preferably 2-4% of micronized prasugrel base, 40-80%, preferably 60-80% of a filler, 2-20% preferably 5-10% of a binder, 2-20% preferably 5-10% disintegrating agent, 5-20% of starch or a starch derivative, preferably 1-3% of a sliding agent and optionally 0.1-2% of a glidant.

According to the most preferable embodiment of the present invention there are provided tablets comprising 2-5% preferably 2-4% of micronized prasugrel base, 40-80% preferably 60-80% of microcrystalline cellulose, 2-20% preferably 5-10% of hypermellose, 2-20% preferably 5-10% by weight of croscarmellose sodium salt, 5-20% of pre-gelatinized starch, 1-3% of sodium stearyl sulfate and optionally 0.1-2% of colloidal silicium dioxide.

In one embodiment, the pharmaceutical compositions of the invention contain only micronized prasugrel base, and a starch or starch derivative as mandatory ingredients. However, in such embodiments, the composition does not contain sodium lauryl sulphate and/or magnesium stearate. Optionally, said embodiments also do not contain fumaric acid. Optionally, the composition contains sodium stearyl fumarate or stearic acid. Furthermore, preferably, the micronized prasugrel base is not co-micronized with other ingredients, e.g., starch. In yet another embodiment of the invention, certain ingredients may be excluded: surfactants; mannitol, lactose and the like; pH regulators, e.g., organic acids, and also sodium lauryl sulphate and/or magnesium stearate.

Furthermore a few process features may also be e.g., all kinds of solvent-free technologies like compaction or dry granulation, direct compression, melt technologies, for example, as disclosed in WO 2010/094471 where such processes are widely used.

In another embodiment, the prasugrel base is micronized without any other ingredients, i.e., the prasugrel base is not co-micronized, e.g., with starch or cellulose, etc. Co-milling can lead to unforeseen differences in the milled product mixture, leading to qualitative differences in the final milled product (due to losses of one of the ingredients during co-grinding). This may cause a quality assurance problem then as different materials produce different losses. So, one cannot foresee the exact composition of the co-milled material and may not be able to predict its dissolution. Surprisingly, according to a preferred embodiment of the present invention, there is no need for co-milling with any kind of excipients.

In a further embodiment of the invention, the prasugrel base is however not micronized.

According to a further aspect of the present invention there is provided a process for the preparation of prasugrel base containing solid pharmaceutical compositions which comprises granulating the components of the internal phase, a part or the complete amount of the filler and the starch or starch derivative with the aqueous solution of the binder, drying the granules obtained, admixing the dry granules with the components of the external phase, the micronized prasugrel base, the remaining portion of the filler, the disintegrating agents and the glidants, homogenizing the mixture and if desired pressing into tablets or filling in capsules. The tablets can be optionally coated.

In a preferred embodiment of preparation, the starch or starch derivative is dispersed/dissolved in a binder/granulating solution. In a more preferred embodiment, the starch is dissolved/dispersed in purified water together with hypromellose, for example, as exemplified in Example 2. Said solution thereafter is sprayed onto fluidized microcrystalline cellulose and hypromellose, which is thereafter dried to yield granules. The granules thereafter are brought together with additional ingredients, i.e., the micronized prasugrel, which has been micronized without any additional ingredients, and with either sodium stearyl fumarate or stearic acid, and other optional ingredients, for example, as provided in example 2.

The prasugrel containing pharmaceutical composition according to the present invention can be administered simultaneously with aspirin for the prevention of atherothrombolytic events of patients suffering from acute coronary syndrome who were subjected to percutant coronary intervention. Acute coronary syndrome is a disease group comprising unstable angina/a serious type of thoracic pain and heart attack. Percutaneous coronary intervention is a type of surgery which makes the tapered coronary artery/the vessels of the heart/penetrable.

In sum, without limiting the invention, the invention relates to the following preferred aspects in any combination of said aspects.

In a 1-st aspect, the invention relates to a pharmaceutical composition comprising
micronized prasugrel base,
starch or starch derivative, and
sodium stearyl fumarate or stearic acid.

In a 2-nd aspect, the invention relates to a pharmaceutical composition wherein the starch or starch derivative is pre-gelatinized starch.

In a 3-rd aspect, the invention relates to a pharmaceutical composition wherein only the prasugrel base is micronized.

In a 4-th aspect, the invention relates to a pharmaceutical composition wherein the composition is in tablet form.

In a 5-th aspect, the invention relates to a pharmaceutical composition in a table form wherein the tablet has a hardness of from 50 to 150, as determined by a (Pharmatron hardness tester) or (following the guidelines set by the FDA/European medicines agency regulations) and/or
the tablet has a friability rating of at most 0.30% as determined by a (Pharmatron FR friability tester) or (following the guidelines set by FDA/European medicines agency regulations) and/or
the tablet has an average disintegration rate in water of below 3 minutes, as determined by a (Pharmatron DTG disintegration tester) or (following the guidelines set by the FDA/European medicines agency regulations) and an average dissolution rate in 900 ml, 0.05 M citrate/phosphate buffer, pH=4.00±0.05 of above 80% in 30 minutes, as determined by a (Pharmatron DIS 8000 dissolution tester) or (following the guidelines set by FDA/European medicines agency regulations), and/or
the tablet retains at least 90% potency, as defined by FDA/European medicines agency regulations, 60 days from manufacture under ambient conditions.

In a 6-th aspect, the invention relates to a pharmaceutical composition wherein the composition contains no surfactants or pH regulators.

In a 7-th aspect, the invention relates to a pharmaceutical composition wherein the composition contains no mannitol, lactose, organic acids, magnesium stearate, HCL, hydrogen sulphate, sodium lauryl sulphate, xylitol or fumaric acid.

In an 8-th aspect, the invention relates to a pharmaceutical composition wherein the starch is not sodium starch glycolate.

In a 9-th aspect, the invention relates to a pharmaceutical composition wherein the composition is substantially free of a prasugrel salt.

In a 10-th aspect, the invention relates to a pharmaceutical composition wherein the starch comprise 5%-20% by weight of the total composition.

In an 11-th aspect, the invention relates to a pharmaceutical composition wherein the micronized prasugrel base comprises 2%-5% by weight of the total composition.

In a 12-th aspect, the invention relates to a pharmaceutical composition wherein the sodium stearyl fumarate or stearic acid comprises 1%-3% by weight of the total composition.

In a 13-th aspect, the invention relates to a pharmaceutical composition wherein the size of the micronized prasugrel base particles are below 10 µm, preferably 2-6 µm, more preferably 3-5 µm.

In a 14-th aspect, the invention relates to a pharmaceutical composition consisting essentially of:
micronized prasugrel base,
starch or starch derivative, and
sodium stearyl fumarate or stearic acid.

In a 15-th aspect, the invention relates to a method of treating atherothrombotic events of patients suffering from acute coronary syndrome in which patients were subjected to percutaneous coronary intervention, said method comprising:
administering an effective amount of a composition which comprises a pharmaceutical composition as disclosed herein, e.g., Prasugrel base containing solid pharmaceutical composition comprising micronized prasugrel base, starch or starch derivative, and sodium stearyl fumarate or stearic acid to a subject in need thereof.

In a 16-th aspect, the invention relates to a pharmaceutical composition prepared by a process comprising:
granulating prasugrel base of less than 10 um in size with an aqueous solution
drying the granules thus obtained, and
admixing the dry granules with a starch or starch derivative and sodium stearyl fumarate or stearic acid.

In a 17-th aspect, the invention relates to a pharmaceutical composition wherein the resulting mixture, e.g., from aspect 16, is pressed into tablets.

In an 18-th aspect, the invention relates to a pharmaceutical composition comprising:
micronized prasugrel base, which has been micronized without any further ingredients; and
a starch or starch derivative, and
optionally sodium stearyl fumarate or stearic acid,
wherein, the composition does not contain sodium lauryl sulphate and magnesium stearate, and the composition is substantially free of a prasugrel salt.

In a 19-th aspect, the invention relates to a pharmaceutical composition wherein the composition of aspect 18 is in tablet form.

Further details of the present invention are to be found in the following Examples without limiting the scope of protection to said Examples.

Example 1

Tablets comprising prasugrel

A. Composition

| | Compound | Prasugrel film tablet 5 mg | Prasugrel film tablet 10 mg |
|---|---|---|---|
| Tablet core | Micronized prasugrel base (Prasugrel) | 5.00 mg | 10.00 mg |
| | Ac-Di-Sol DS 711 (Croscarmellose sodium) | 20.00 mg | 40.00 mg |
| | Microcrystalline cellulose PH 113 FMC (Cellulose, microcrystalline) | 16.00 mg | 32.00 mg |
| | Microcrystalline cellulose PH 101 (Cellulose, microcrystalline) | 125.00 mg | 250.00 mg |

| | Compound | Prasugrel film tablet 5 mg | Prasugrel film tablet 10 mg |
|---|---|---|---|
| | Hypromellose 2910, 6 cP (Hypromellose) | 10.00 mg | 20.00 mg |
| | Corn starch Starch 1500 (Starch, pregelatinized) | 20.00 mg | 40.00 mg |
| | Sodium stearil fumarate | 4.00 mg | 8.00 mg |
| Film coating | Tablet core: | 200.00 mg | 400.00 mg |
| | Opadry II. 33G28523 White | 6.00 mg | 12.00 mg |
| | Film coated tablet: | 206.00 mg | 412.00 mg |

Composition of the Opadry II 33G28523 White Coating
The composition of Opadry II. 33G28523 white:

| Hypromellose | 40.00% |
|---|---|
| Titanium dioxide | 25.00% |
| Lactose monohydrate | 21.00% |
| Macrogol 3350 | 8.00% |
| Glycerol triacetate | 6.00% |

B. Short Description of the Manufacturing Process
I. Granulation
Preparation of the Granulating Liquid

| Component | Amount /g/ |
|---|---|
| Hypromellose 2910 6 cP | 100.0 g |
| Purified water | 1172.0 g |

Composition of the Internal Phase

| Component | Amount /g/ |
|---|---|
| Microcrystalline cellulose | 1250 g |
| Starch 1500 | 200 g |

First the granulating solution is prepared. The hypromellose is dissolved in the purified water under stirring. In a Glatt GPCG 3.1 apparatus the hypromellose solution is sprayed on the fluidized microcrystalline cellulose and the Starch 1500. The wet substance is then dried/drying loss 2-2.2%, measured at 90° C. after 10 minutes.

Addition rate of the granulating solution: about 50 g/minute

Temperature of the introduced air: 60° C. during granulation, 75° C. during drying.

From the granules prepared batches of 500 g each are used for the preparation of the next homogenized mixture.

2. Homogenization

| Compound | % | g |
|---|---|---|
| Micronized prasugrel base | 2.50% | 16.13 g |
| Ac-Di-Sol DS 711 | 10.00% | 64.52 g |

-continued

| Compound | % | g |
|---|---|---|
| Cellulose, microcrystalline PH 113 FMC Granules | 8.00% | 51.62 g |
| Cellulose. microcrystalline PH 101 | 62.50% | 500.00 g |
| Hypromellose 2910. 6CP | 5.00% | |
| Corn starch Starch 1500 | 10.00% | |
| Sodium stearyl fumarate | 2.00% | 12.90 g |
| Sum: | 100.00% | 645.2 g |

51.62 g Avicel PH 113 are manually homogenized with 16.13 g of micronized

Prasugrel base and thereafter with 64.52 g of Ac-Di-Sol. The powder mixture is sieved on a 0.5 mm manual sieve.

To the powder mixture 500 g of the granules are added and the mixture is homogenized in a Pharmatech MB 30 mixer at 17 rpm for 8 minutes 12.90 of Pruv are manually homogenized with a small portion of the powder mixture whereupon the mixture is sieved on a 0.5 mm manual sieve. Final homogenization is carried out in a MB 30 mixer at 17 rpm for 2 minutes.

Tableting is carried out on a Korsch XM 12 rotating tableting machine.

Parameters of the tablet:

Prasugrel 5 mg: weight of tablet 200 mg, biconvex form of diameter 9 mm Prasugrel 10 mg, weight of tablet 400 mg, biconvex form of diameter 11 mm.

Film Coating

Preparation of the Coating Dispersion

| Component | Amount |
|---|---|
| Opadry II 33G28523 White | 25.0 g |
| Purified water | 100.0 g |

The Opadry II 33G28523 White is added in small portions under stirring to the purified water. The system is stirred for 45 minutes whereupon it is sieved on a 0.5 mm sieve. 500 g of the tablet core are coated in a Lodige LHC 30 type film coating apparatus. The weight gain of the cores is 6 mg/tablet core/for 5 mg tablets/and 12 mg/tablet core/for 10 mg tablets/, respectively.

| Coating parameters | |
|---|---|
| Temperature of inlet air | 55-65° C. |
| Addition rate | 5-7 g/minute |
| Temperature of outlet air | 40-45° C. |
| Pressure of spraying air | 2.5 bar |
| Rpm of the drum during coating | 14 l/minute |
| Pressure of drum during heating/drying | 3 l/minute |
| Drying | 10 minutes/40° C. |

Tablets Comprising Prasugrel

A. Composition

| Compound | Prasugrel film tablet 5 mg | Prasugrel film tablet 10 mg |
|---|---|---|
| Tablet core | | |
| Micronized prasugrel base (Prasugrel) | 5.00 mg | 10.00 mg |
| Ac-Di-Sol DS 711 (Croscarmellose sodium) | 20.00 mg | 40.00 mg |
| Microcrystalline cellulose PH 113 FMC (Cellulose, microcrystalline) | 16.00 mg | 32.00 mg |
| Microcrystalline cellulose PH 101 (Cellulose, microcrystalline) | 125.00 mg | 250.00 mg |
| Hypromellose 2910, 6 cP (Hypromellose) | 10.00 mg | 20.00 mg |
| Corn starch Starch 1500 (Starch, pregelatinized) | 20.00 mg | 40.00 mg |
| Sodium stearil fumarate | 4.00 mg | 8.00 mg |
| Tablet core: | 200.00 mg | 400.00 mg |
| Film-coating | | |
| Opadry II. 33G28523 White | 6.00 mg | 12.00 mg |
| Film coated tablet: | 206.00 mg | 412.00 mg |

Composition of the Opadry II 33G28523 White Coating

| The composition of Opadry II. 33G28523 white: | |
|---|---|
| Hypromellose | 40.00% |
| Titanium dioxide | 25.00% |
| Lactose monohydrate | 21.00% |
| Macrogol 3350 | 8.00% |
| Glycerol triacetate | 6.00% |

B. Short description of the manufacturing process

I. Granulation

Preparation of the Granulating Liquid

| Component | Amount /g/ |
|---|---|
| Hypromellose 2910 6 cP | 40.0 g |
| Starch 1500 | 200.0 g |
| Purified water | 1360.0 g |

Composition of the Internal Phase

| Component | Amount /g/ |
|---|---|
| Microcrystalline cellulose | 1250.0 g |
| Hypromellose 2910 6 cP | 60.0 g |

First the granulating solution is prepared. The hypromellose and Starch 1500 are dispersed in the purified water under stirring. In a Glatt GPCG 3.1 apparatus the granulation fluid is sprayed on the fluidized microcrystalline cellulose and the hypromellose. The wet substance is then dried/drying loss 2-2.2%, measured at 90° C. after 10 minutes.

Addition rate of the granulating solution: about 50 g/minute

Temperature of the introduced air: 60° C. during granulation, 75° C. during drying.

From the granules prepared batches of 500 g each are used for the preparation of the next homogenized mixture.

2. Homogenization

| Compound | % | g |
|---|---|---|
| Micronized prasugrel base | 2.50% | 16.13 g |
| Ac-Di-Sol DS 711 | 10.00% | 64.52 g |
| Cellulose, microcrystalline PH 113 FMC | 8.00% | 51.62 g |
| Granules | | |
| Cellulose. microcrystalline PH 101 | 62.50% | 500.00 g |
| Hypromellose 2910. 6CP | 5.00% | |
| Corn starch Starch 1500 | 10.00% | |
| Sodium stearyl fumarate | 2.00% | 12.90 g |
| Sum: | 100.00% | 645.2 g |

51.62 g Avicel PH 113 are manually homogenized with 16.13 g of micronized Prasugrel base and thereafter with 64.52 g of Ac-Di-Sol. The powder mixture is sieved on a 0.5 mm manual sieve.

To the powder mixture 500 g of the granules are added and the mixture is homogenized in a Pharmatech MB 30 mixer at 17 rpm for 8 minutes 12.90 of Pruv are manually homogenized with a small portion of the powder mixture whereupon the mixture is sieved on a 0.5 mm manual sieve. Final homogenization is carried out in a MB 30 mixer at 17 rpm for 2 minutes.

Tableting is carried out on a Korsch XM 12 rotating tableting machine.

Parameters of the tablet:

Prasugrel 5 mg: weight of tablet 200 mg, biconvex form of diameter 9 mm. Prasugrel 10 mg, weight of tablet 400 mg, biconvex form of diameter 11 mm.

3. Film Coating

Preparation of the Coating Dispersion

| Component | Amount |
|---|---|
| Opadry II 33G28523 White | 25.0 g |
| Purified water | 100.0 g |

The Opadry II 33G28523 White is added in small portions under stirring to the purified water. The system is stirred for 45 minutes whereupon it is sieved on a 0.5 mm sieve. 500 g of the tablet core are coated in a Lodige LHC 30 type film coating apparatus. The weight gain of the cores is 6 mg/tablet core/for 5 mg tablets/and 12 mg/tablet core/for 10 mg tablets/, respectively.

Coating Parameters

| Coating parameters | |
|---|---|
| Temperature of inlet air | 55-65° C. |
| Addition rate | 5-7 g/minute |
| Temperature of outlet air | 40-45° C. |
| Pressure of spraying air | 2.5 bar |
| Rpm of the drum during coating | 14 l/minute |
| Pressure of drum during heating/drying | 3 l/minute |
| Drying | 10 minutes/40° C. |

Data of dissolution graph of the prasugrel base containing composition according to Example are on FIG. 2:

EXAMPLE 3

One proceeds according to the preceding example except that to the external phase of the tablet additionally the colloidal silica is added.

Composition of the Tablet Core

| Component | Interval |
|---|---|
| Tablet core | |
| Micronized prasugrel base (Prasugrel) | 2.50% |
| Ac-Di-Sol DS 711 (Croscarmellose sodium) | 5.00% |
| Cellulose, microcrystalline PH 102 | 63.80% |
| Cellulose, microcrystalline PH 113 FMC | 11.50% |
| Hypromellose 2910, 6 cP | 5.00% |
| Corn starch Sta-RX 1500 Starch, pregelatinized | 10.00% |
| Nátrium-stearil-fumarát Sodium stearil fumarate | 2.00% |
| Aerosol R972 | 0.20% |

Data of Dissolution Graph of the Prasugrel Base Containing Composition According to Example 1.

The conditions of the dissolution graph/FIG. 1/:

The test was carried out in 900 ml of sodium lauryl sulphate free citrate buffer of pH 4, used a paddle stirrer at 75 rpm.

| | | Example 5 | | | | | | |
|---|---|---|---|---|---|---|---|---|
| | | 5 | 15 | 30 | 45 | 60 | 75 | 90 |
| Test tablet containing 10 mg | Prasugrel | 36.30 | 81.19 | 88.56 | 90.13 | 89.71 | 88.96 | 87.51 |
| | Desacetil deriv. | 0.07 | 1.29 | 3.14 | 4.77 | 6.70 | 8.32 | 10.46 |

-continued

| | | Example 5 | | | | | | |
|---|---|---|---|---|---|---|---|---|
| | | 5 | 15 | 30 | 45 | 60 | 75 | 90 |
| Prasugrel base | Sum: | 36.37 | 82.48 | 91.70 | 94.90 | 96.40 | 97.29 | 97.96 |
| | SD | 5.15 | 0.90 | 0.72 | 0.75 | 0.90 | 0.93 | 1.03 |
| | RSD[%] | 14.17 | 1.09 | 0.78 | 0.79 | 0.93 | 0.96 | 1.05 |
| Effient 10 mg A803532A | Prasugrel | 59.70 | 78.40 | 84.30 | 85.20 | 84.90 | 83.90 | 83.10 |
| | Desacetil deriv. | 1.10 | 2.60 | 4.40 | 6.60 | 8.40 | 10.50 | 12.60 |
| | Sum | 60.80 | 81.00 | 88.80 | 91.80 | 93.30 | 94.40 | 95.70 |
| | SD | 1.17 | 1.27 | 1.52 | 1.53 | 1.72 | 1.70 | 1.78 |
| | RSD[%] | 1.92 | 1.57 | 1.71 | 1.67 | 1.84 | 1.80 | 1.86 |

Examination of the Bioavailability of the Composition According to Example 1 Together with Lansoprasole Treatment Bioequivalence of Prasugrel 10 mg tablets of Example 1 and Effient™ 10 mg tablets (Eli Lilly and Company, USA) following administration of 30 mg dose was investigated in a single dose, 2-period, 2-treatment, 2-sequence crossover study in healthy subjects taking lansoprazole for at least 1 week under fasting condition. Thirty male non smoker healthy volunteers were randomly assigned to a treatment sequence and received two separate single 30 mg (3×10 mg tablets) dose administration of investigational medications following 7-day lansoprazole pretreatment according to a randomized schedule. Subjects fasted overnight for at least 10 hours prior to prasugrel administration. Blood samples were collected prior to prasugrel administration and 0.17, 0.33, 0.5, 0.75, 1, 1.25, 1.5, 1.75, 2, 2.5, 3, 4, 6, 8, 12 and 24 hours after prasugrel administration. The samples were analyzed for main inactive metabolite (R-95913), and main active metabolite of prasugrel (R-138727) by validated HPLC-MS/MS method and the following pharmacokinetic parameters were calculated: $C_{max}$, $AUC_T$, $AUC_\infty$, $AUC_{T/\infty}$, $K_{el}$ and $T_{1/2el}$. Statistical analysis of bioequivalence was based on a parametric ANOVA model and two-sided 90% confidence interval of the ratio of geometric means for the ln-transformed $C_{max}$, $AUC_T$ and $AUC_\infty$. Bioequivalence was concluded if the 90% geometric confidence intervals of the test/reference ratio of least-squares means for ln-transformed $C_{max}$, $AUC_T$, and $AUC_\infty$ were within the acceptable range of 80.00% to 125.00% for the main inactive metabolite (R-95913) of prasugrel. Statistical analysis of the active metabolite of prasugrel (R-138727) was performed for supportive purpose.

The results provided in Table 1 and Table 2 bellow indicate that the Test to Reference ratio of geometric LSmeans and corresponding 90% confidence interval for the $C_{max}$, $AUC_T$ and $AUC_\infty$ were all within the acceptance range of 80.00 to 125.00% for both R-95913 and R-138727.

TABLE 1

Statistical comparison of the relative bioavailability of R-95913 between the Test (T) and the Reference (R) formulation

| PARAMETER | INTRA-SUBJECT C.V. (%) | GEOMETRIC LSMEANS * | | T/R RATIO (%) | 90% CONFIDENCE LIMITS (%) | |
|---|---|---|---|---|---|---|
| | | TEST | REFERENCE | | LOWER | UPPER |
| $C_{max}$ | 23.4 | 64.398 | 68.238 | 94.37 | 85.26 | 104.46 |
| $AUC_T$ | 13.3 | 184.807 | 188.328 | 98.13 | 92.58 | 104.02 |
| $AUC_\infty$ | 13.3 | 195.887 | 201.992 | 96.98 | 91.48 | 102.80 |

* units are ng/mL for $C_{max}$ and ng · h/mL for $AUC_T$ and $AUC_\infty$

TABLE 2

Statistical comparison of the relative bioavailability of R-138727 between the Test (T) and the Reference (R) formulation

| PARAMETER | INTRA-SUBJECT C.V. (%) | GEOMETRIC LSMEANS * | | T/R RATIO (%) | 90% CONFIDENCE LIMITS (%) | |
|---|---|---|---|---|---|---|
| | | TEST | REFERENCE | | LOWER | UPPER |
| $C_{max}$ | 37.1 | 82.974 | 83.015 | 99.95 | 85.37 | 117.02 |
| $AUC_T$ | 13.0 | 136.178 | 135.809 | 100.27 | 94.71 | 106.15 |
| $AUC_\infty$ | 13.3 | 139.838 | 139.927 | 99.94 | 94.30 | 105.91 |

* units are ng/mL for $C_{max}$ and ng · h/mL for $AUC_T$ and $AUC_\infty$

Administering with proton pump inhibitor lansoprazole, Prasugrel formulation of Example 1 containing prasugrel base and Effient™ formulation was bioequivalent under fasting condition based on both the main inactive metabolite (R-95913) and the main active metabolite (R-138727).

EXAMPLE 6

Examination of the Bioavailability of the Composition According to Example 1 Under Fed Condition The bioequivalence of Prasugrel 10 mg tablets of Example 1 and Effient™ 10 mg tablets (Eli Lilly and Company, USA) following administration of 30 mg dose was investigated in a single dose, 2-period, 2-treatment, 2-sequence crossover study in healthy subjects under fed condition. Twenty-four male non smoker healthy volunteers were randomly assigned to a treatment sequence and received two separate single 30 mg (3×10 mg tablets) dose administration of investigational medications according to a randomized schedule. Following an overnight fast of at least 10 hours, subjects received a high-fat, high-calorie breakfast 30 minutes prior to drug administration. Blood samples were collected prior to prasugrel administration and 0.17, 0.33, 0.5, 0.75, 1, 1.25, 1.5, 1.75, 2, 2.5, 3, 4, 6, 8, 12 and 24 hours after prasugrel administration. The samples were analyzed for main inactive metabolite (R-95913), and main active metabolite of prasugrel (R-138727) and the following pharmacokinetic parameters were calculated: $C_{max}$, $AUC_T$, $AUC_\infty$, $AUC_{T/\infty}$, $K_{el}$ and $T_{1/2el}$. Analysis of variance Statistical analysis of bioequivalence was based on a parametric ANOVA model and two-sided 90% confidence interval of the ratio of geometric means for the ln-transformed $C_{max}$, $AUC_T$ and $AUC_\infty$. Bioequivalence was concluded if the 90% geometric confidence intervals of the test/reference ratio of least-squares means for ln-transformed $C_{max}$, $AUC_T$ and $AUC_\infty$ were within the acceptable range of 80.00% to 125.00% for the main inactive metabolite (R-95913) of prasugrel. Statistical analysis of the active metabolite of prasugrel (R-138727) was performed for supportive purpose.

The results provided in Table 3. and Table 4. bellow indicate that the Test to Reference ratio of geometric LSmeans and corresponding 90% confidence interval for the $C_{max}$, $AUC_T$ and $AUC_\infty$ were all within the acceptance range of 80.00 to 125.00% for both R-95913 and R-138727.

TABLE 3

Statistical comparison of the relative bioavailability of R-95913 between the Test (T) and the Reference (R) formulation

| PARAMETER | INTRA-SUBJECT C.V. (%) | GEOMETRIC LSMEANS * TEST | GEOMETRIC LSMEANS * REFERENCE | T/R RATIO (%) | 90% CONFIDENCE LIMITS (%) LOWER | 90% CONFIDENCE LIMITS (%) UPPER |
|---|---|---|---|---|---|---|
| $C_{max}$ | 27.6 | 84.095 | 89.703 | 93.75 | 81.98 | 107.21 |
| $AUC_T$ | 12.9 | 272.240 | 284.447 | 95.71 | 89.82 | 101.99 |
| $AUC_\infty$ | 12.6 | 283.388 | 296.153 | 95.69 | 89.91 | 101.84 |

* units are ng/mL for $C_{max}$ and ng · h/mL for $AUC_T$ and $AUC_\infty$

TABLE 4

Statistical comparison of the relative bioavailability of R-138727 between the Test (T) and the Reference (R) formulation

| PARAMETER | INTRA-SUBJECT C.V. (%) | GEOMETRIC LSMEANS * TEST | GEOMETRIC LSMEANS * REFERENCE | RATIO (%) | 90% CONFIDENCE LIMITS (%) LOWER | 90% CONFIDENCE LIMITS (%) UPPER |
|---|---|---|---|---|---|---|
| $C_{max}$ | 34.2 | 66.585 | 69.843 | 95.34 | 80.84 | 112.43 |
| $AUC_T$ | 6.4 | 142.963 | 149.431 | 95.67 | 92.69 | 98.75 |
| $AUC_\infty$ | 6.4 | 146.990 | 153.439 | 95.80 | 92.80 | 98.90 |

* units are ng/mL for $C_{max}$ and ng · h/mL for $AUC_T$ and $AUC_\infty$

Prasugrel formulation of Example 1 containing prasugrel base and Effient™ formulation was bioequivalent under fed condition based on both the main inactive metabolite (R-95913) and the main active metabolite (R-138727).

Figure 1:
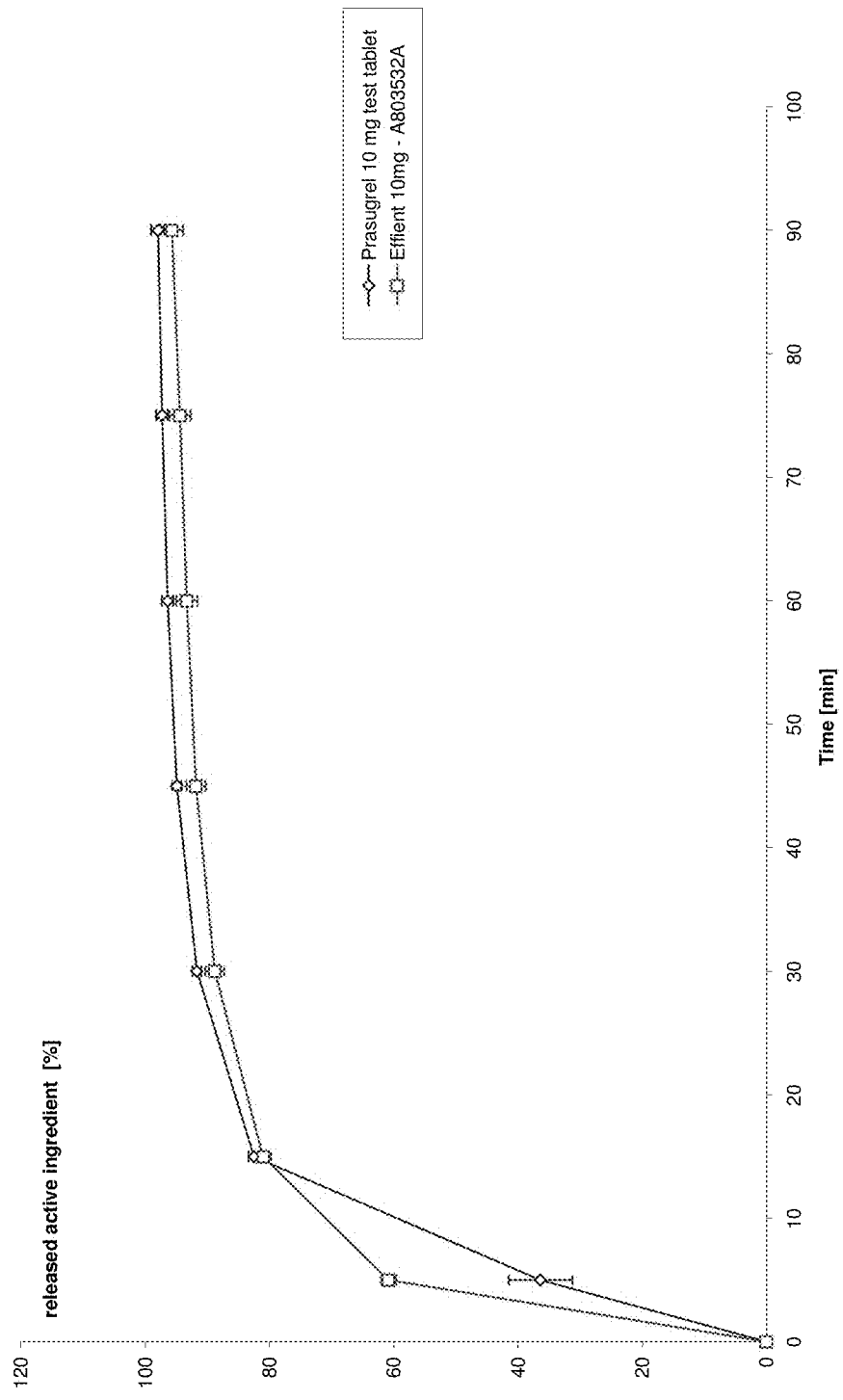
FIG. 1 illustrates a dissolution graph.
Figure 2:
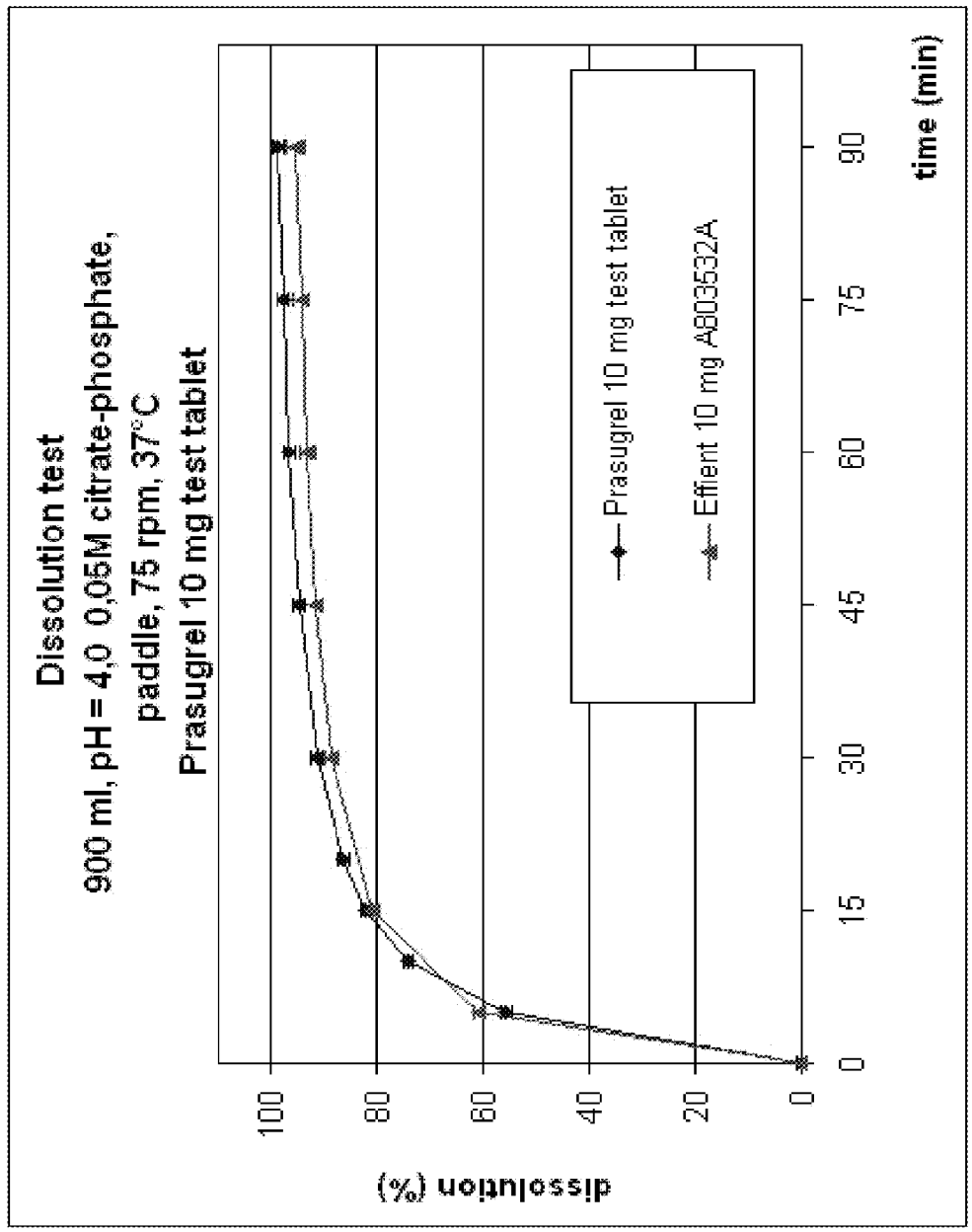
FIG. 2 illustrates a dissolution graph, Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein are incorporated by reference herein.

The invention claimed is:

1. A pharmaceutical composition comprising:
an internal phase and an external phase, wherein the internal phase is in the form of granules and the external phase is present around and between the granules of said internal phase, wherein
the granulated internal phase comprises starch or a starch derivative, and
the external phase comprises a micronized prasugrel base and at least one further auxiliary agent,
wherein prasugrel means (5-/2-cyclopropyl-1-(2-fluorophenyl)-2-oxoethyl/-4,5,6,7-tetrahydrothieno/3.2-c/-pyridine-2-yl-acetate.

2. The composition of claim 1, wherein the starch or starch derivative is a pre-gelatinized starch.

3. The composition of claim 1, wherein the external phase of the composition comprises as auxiliary agent sodium stearyl fumarate or stearic acid.

4. The composition of claim 1, wherein the composition is in tablet form.

5. The composition of claim 4, wherein the tablet has a hardness of from 50 to 150 N, as determined by a (Pharmatron hardness tester) or (following the guidelines set by the FDA/European medicines agency regulations), and/or
the tablet has a friability rating of at most 0.30% as determined by a (Pharmatron FR friability tester) or (following the guidelines set by FDA/European medicines agency regulations), and/or
the tablet has an average disintegration rate in water of below 3 minutes, as determined by a (Pharmatron DTG disintegration tester) or (following the guidelines set by the FDA/European medicines agency regulations) and an average dissolution rate in 900 ml, 0.05 M citrate/phosphate buffer, pH=4.00±0.05 of above 80% in 30 minutes, as determined by a (Pharmatron DIS 8000 dissolution tester) or (following the guidelines set by FDA/European medicines agency regulations), and/or
the tablet retains at least 90% potency, as defined by FDA/European medicines agency regulations, 60 days from manufacture under ambient conditions.

6. The composition of claim 4, wherein the tablet has a hardness of from 50 to 150 N, as determined by a (Pharmatron hardness tester), and/or
the tablet has a friability rating of at most 0.30% as determined by a (Pharmatron FR friability tester), and/or
the tablet has an average disintegration rate in water of below 3 minutes, as determined by a (Pharmatron DTG disintegration tester) and an average dissolution rate in 900 ml, 0.05 M citrate/phosphate buffer, pH=4.00±0.05 of above 80% in 30 minutes, as determined by a (Pharmatron DIS 8000 dissolution tester), and/or
the tablet retains at least 90% potency 60 days from manufacture under ambient conditions.

7. The composition of claim 1, wherein the composition contains no surfactants or pH regulators.

8. The composition of claim 1, wherein the composition contains no mannitol, lactose, organic acids, magnesium stearate, HCL, hydrogen sulphate, sodium lauryl sulphate, xylitol or fumaric acid.

9. The composition of claim 1, wherein the starch is not sodium starch glycolate.

10. The composition of claim 1, wherein the composition is free of a prasugrel salt.

11. The composition of claim 1, wherein the starch is 5%-20% by weight of the total composition.

12. The composition of claim 1, wherein the micronized prasugrel base is 2%-5% by weight of the total composition.

13. The composition of claim 1, wherein the sodium stearyl fumarate or stearic acid is 1%-3% by weight of the total composition.

14. The composition of claim 1, wherein the size of the micronized prasugrel base particles are below 10 μm.

15. A pharmaceutical composition according to claim 1, consisting essentially of:
starch or a starch derivative placed in the internal phase, and
a micronized prasugrel base in the external phase.

16. A pharmaceutical composition having an internal phase and an external phase, wherein the internal phase is in the form of granules and the external phase is present around and between the granules of said internal phase, which composition is prepared by a process comprising:
granulating the internal phase comprising starch or a starch derivative with an aqueous solution of a binder, drying the granules obtained, admixing the dry granules with a micronized prasugrel base which forms the external phase, homogenizing the mixture, and optionally pressing into tablets or filling in capsules,
wherein prasugrel means (5-/2-cyclopropyl-1-(2-fluorophenyl)-2-oxoethyl/-4,5,6,7-tetrahydrothieno/3.2-c/-pyridine-2-yl-acetate.

17. A pharmaceutical composition prepared by a process according to claim 16, wherein the internal phase comprises a part or the complete amount of a filler and the starch or starch derivative, and the external phase comprises the micronized prasugrel base, the remaining portion of the filler, and one or more disintegrating agents and glidants.

18. The pharmaceutical composition of claim 16, wherein the resulting mixture is pressed into tablets.

19. A pharmaceutical composition comprising:
   an internal phase and an external phase, wherein the internal phase is in the form of granules and the external phase is present around and between the granules of said internal phase, wherein
   a micronized prasugrel base, which has been micronized without any further ingredients is in the external phase and starch or a starch derivative is in the internal phase, and optionally sodium stearyl fumarate or stearic acid, wherein the composition does not contain sodium lauryl sulphate and magnesium stearate, and the composition is free of a prasugrel salt,
   wherein prasugrel means (5-/2-cyclopropyl-1-(2-fluorophenyl)-2-oxoethyl/-4,5,6,7-tetrahydrothieno/3.2-c/-pyridine-2-yl-acetate.

20. The composition of claim 19, wherein the composition is in tablet form.

* * * * *